United States Patent
Jüsten et al.

(10) Patent No.: US 9,636,290 B2
(45) Date of Patent: May 2, 2017

(54) USE OF A NOVEL NATURAL AGENT IN COSMETIC COMPOSITIONS

(75) Inventors: Peter Jüsten, Rueil-Malmaison (FR); Dominique Marie Noëlle Borreill, Chennevieres sur Marne (FR)

(73) Assignee: LESAFFRE ET COMPAGNIE, Paris (FR)

( * ) Notice: Subject to any disclaimer, the term of this patent is extended or adjusted under 35 U.S.C. 154(b) by 987 days.

(21) Appl. No.: 12/679,777

(22) PCT Filed: Sep. 23, 2008

(86) PCT No.: PCT/FR2008/001319
§ 371 (c)(1),
(2), (4) Date: Jun. 3, 2010

(87) PCT Pub. No.: WO2009/074735
PCT Pub. Date: Jun. 18, 2009

(65) Prior Publication Data
US 2011/0034393 A1    Feb. 10, 2011

(30) Foreign Application Priority Data
Sep. 25, 2007   (FR) .................................... 07 06701

(51) Int. Cl.
| | | |
|---|---|---|
| *A61K 38/02* | (2006.01) | |
| *A61P 17/10* | (2006.01) | |
| *A61P 17/08* | (2006.01) | |
| *A61P 17/00* | (2006.01) | |
| *A61Q 5/00* | (2006.01) | |
| *A61Q 19/08* | (2006.01) | |
| *A61Q 19/00* | (2006.01) | |
| *A61K 8/64* | (2006.01) | |
| *A61K 8/99* | (2017.01) | |
| *A61Q 7/00* | (2006.01) | |
| *A61K 38/16* | (2006.01) | |

(52) U.S. Cl.
CPC .................. *A61K 8/64* (2013.01); *A61K 8/99* (2013.01); *A61K 38/16* (2013.01); *A61Q 5/00* (2013.01); *A61Q 5/006* (2013.01); *A61Q 7/00* (2013.01); *A61Q 19/00* (2013.01); *A61Q 19/008* (2013.01); *A61Q 19/08* (2013.01); *A61K 2800/48* (2013.01)

(58) Field of Classification Search
CPC combination set(s) only.
See application file for complete search history.

(56) References Cited

U.S. PATENT DOCUMENTS

| | | |
|---|---|---|
| 5,739,102 A | 4/1998 | Batterbury et al. |
| 2004/0054166 A1 | 3/2004 | Sauter et al. |
| 2004/0067544 A1 | 4/2004 | Vogel et al. |
| 2006/0078568 A1 | 4/2006 | Pauly et al. |
| 2006/0194760 A1* | 8/2006 | Griesbach et al. ............. 514/54 |

FOREIGN PATENT DOCUMENTS

| | | |
|---|---|---|
| JP | 2008222655 | 9/2008 |
| WO | WO/2007/135390 | 11/2007 |

OTHER PUBLICATIONS

Components of the Bioemulsifier From S. cerevisiae; Jeffrey A.T. Barriga, David G. Cooper, Edmund S. Idziak, David R. Cameron; Dept. of Chemical Engineering, McGill University, Montreal, Quebec Canada; Department of Natural Resource Sciences (Microbiology Group) McGill University, Ste. Anne de Bellevue, Quebec, Canada; Tembec Inc. Temiscaming, Quebec, Canada; Enzyme and Microbial Technology 25 (1999) pp. 96-102.
Preparation and Characterisation of Bioemulsifier From *Saccharomyces cerevisiae* and Its Application in Food Products; H. Torabizadeh, S.A. Shojaosadati, H.A. Tehrani; Iranian Research Organization for Science and Technology, 71, Forsat Street, Enghelab Avenue, P.O. Box 15815-3538, Tehran 15819 Iran; Biotechnology Group, Tarbiat Modarres University, P.O. Box 14155-4838, Tehran, Iran; pp. 734-737.
The Mannoprotein of *Saccharomyces cerevisiae* is an Effective Bioemulsifier; David R. Cameron, David G. Cooper, Ron J. Neufeld; Department of Chemical Engineering, McGill University, 3480 University Street, Montreal, Quebec, Canada H3A 2A7; Applied and Environmental Microbiology, Jun. 1988, pp. 1420-1425.

\* cited by examiner

*Primary Examiner* — Adam C Milligan
*Assistant Examiner* — Sarah Alawadi
(74) *Attorney, Agent, or Firm* — DeLio, Peterson & Curcio, LLC; Kelly M. Nowak

(57) ABSTRACT

The invention relates to cosmetic or dermatological compositions containing mannoproteins as an active ingredient and/or adjuvant, to the use of said cosmetic or dermatological compositions and to cosmetic treatment methods.

4 Claims, No Drawings

USE OF A NOVEL NATURAL AGENT IN COSMETIC COMPOSITIONS

CROSS REFERENCE TO RELATED APPLICATIONS

This application is a national phase filing of pending International Patent Application PCT/FR2008/001319 filed on Sep. 23, 2008 which designates the United States, and which claims priority of French Patent Application No. FR 0706701 filed on Sep. 25, 2007. The contents of the above mentioned PCT Application and French Application are relied upon and incorporated herein by reference in their entirety.

FIELD OF THE INVENTION

A subject of the present invention is the use of a novel natural agent in cosmetic compositions, as well as in dermatological compositions.

TECHNOLOGICAL BACKGROUND

Mannoproteins are mannans bound to proteins which are found in particular in yeast walls where they have a structural and/or antigenic function.

Mannoproteins are commonly used in oenology, in particular for stabilizing wine (see for example documents WO 96/013571, WO 01/046380 and WO 06/067147). The use of mannoproteins for reducing the haze level of alcoholic beverages is described in application WO 07/034986.

In patent application EP 0 790316, mannoproteins are used as an emulsifier in beverages and food products.

In the application WO 01/066574, the mannoproteins of *cryptococcus neoformans* are used for the preparation of a medicament intended for the treatment of inflammatory diseases or infections, via a method of administration by systemic route. The mannoproteins then make it possible to suppress neutrophil migration.

Moreover, mannoproteins are described as an adjuvant of active ingredients, i.e. as a compound making it possible to improve or reinforce the therapeutic effect of active ingredients.

Thus, in international application US 2005/0226822, mannoproteins are used as ovomucin adjuvants in oral care compositions.

International application WO 06/036817 describes the use of mannoproteins as an adjuvant in a pharmaceutical composition comprising fungal cells or cell extracts genetically modified so as to have at least one altered filamentation property. The immunogenic properties of the mannoproteins are used to improve the immune response of the composition. This application is based on a principle of vaccination against fungal infections due in particular to fungi of the genus *Candida*.

In patent application US 2005/0191268, mannoproteins are used as polyphenol adjuvants in cosmetic preparations comprising an extract of a residue of the winemaking process and one or more cosmetic additives or adjuvants. Said residue is the deposit remaining at the bottom of the vats after the wine is pumped out on completion of fermentation. Said residue extract comprises one or more polyphenols and one or more proteins, for example mannoproteins, as association complexes.

In the cosmetic field, it is useful to have multi-functional agents which make it possible in particular to reduce the range of raw materials necessary for the preparation of different cosmetic compositions and/or to simplify the method for preparing the cosmetic products.

Furthermore, consumers are in search of natural cosmetic products, comprising components of natural origin. It is therefore useful to have natural functional agents for preparing cosmetic products.

SUMMARY OF THE INVENTION

A subject of the present invention is to provide a novel multifunctional natural agent which is useful in the cosmetic or dermatological field.

A subject of the invention is also the provision of novel cosmetic or dermatological compositions.

Another subject of the invention relates to a method for cosmetic or dermatological treatment of the skin and/or skin appendages.

A subject of the present invention is a cosmetic or dermatological composition comprising mannoproteins as active ingredients and/or as additives.

The invention is based on the discovery that mannoproteins are in fact active ingredients as such, without any need to combine them with other components, in particular for a topical application in cosmetic and/or dermatological compositions.

The invention is also based on the discovery that mannoproteins also have texturizing effects in the presence of another texturizing product in these cosmetic and/or dermatological compositions, which can be used advantageously.

DETAILED DESCRIPTION OF EMBODIMENTS

A particular subject of the present invention is a cosmetic or dermatological composition comprising mannoproteins as active ingredients and/or as additives, characterized in that it contains no polyphenols.

A particular subject of the present invention is a composition as defined above characterized in that the mannoproteins originate from yeasts, in particular from yeast of the genus *Saccharomyces, Kluyveromyces, Torula* or *Candida*, preferably *Saccharomyces*.

A particular subject of the present invention is a composition as defined above characterized in that the mannoproteins originate from *Saccharomyces cerevisiae*.

By "cosmetic composition", is meant here a composition intended to procure a cosmetic effect in the context of a topical application.

By "dermatological composition", is meant a composition intended to procure a topical therapeutic effect.

In both cases, the composition comprises, in addition to water and mannoproteins, all of the compounds (in particular excipients and additives) necessary for a cosmetic or dermatological use, as a person skilled in the art will appreciate.

The term "topical" indicates that the composition is active at the point where it is applied to the skin, the skin appendages or mucous membranes. The composition according to the invention can at the same time target the superficial layers of the epidermis, the epidermis, and/or the dermis.

A particular subject of the present invention is a cosmetic or dermatological composition as defined above intended for application to the skin and/or to the skin appendages, excluding the mucous membranes.

By the term "skin appendage", is generally meant anything covering the body, in particular the hair, nails, bristles, eyelashes.

The term "skin" includes the scalp.

The mannoproteins according to the invention are obtained by standard methods well known to a person skilled in the art.

In particular, the mannoproteins are extracted from the cell walls of fungi, in particular from the cell walls of yeast.

The extraction of the mannoproteins from the cell walls can be carried out by selective solubilization of the mannoproteins, via hydrolysis by chemical, enzymatic or physicochemical route. Preferably, the selective solubilization is achieved under the action of temperature.

The insoluble fraction is removed and the solubilized fraction containing the mannoproteins is recovered. The mannoproteins in the soluble fraction can then be precipitated or concentrated and optionally dried.

Preferably, a stage of purification of the mannoproteins is carried out after separation of the insoluble fraction.

A method for obtaining soluble mannoproteins is for example described in patent application EP 1 094117 in the name of the applicant, or also WO-A-96/13571 and WO-A-97/49794.

It is possible to use any type of starting product, and in particular yeast strains. In particular, the mannoproteins originate from *Saccharomyces, Kluyveromyces*, Torula or *Candida. Saccharomyces*, in particular cerevisiae, are preferred.

A particular subject of the present invention is a cosmetic or dermatological composition as defined above, in which the mannoproteins are extracted from yeast walls, said yeasts not having served any use before said extraction of the mannoproteins.

The cosmetic or dermatological compositions according to the invention can be prepared from mannoproteins in dried form, in particular in powder form, or in solution, for example in aqueous solution.

A cosmetic or dermatological composition according to the invention comprises at least one compound as active ingredient, at least one compound as an additive and at least one compound as an excipient, the same compound being able to be used in several ways.

By "active ingredient" is meant here the substance responsible for the cosmetic effect in the case of a cosmetic composition or responsible for the therapeutic effect within the context of a dermatological composition.

By "additive" is meant an agent having in the cosmetic or dermatological composition the role of a preservative, chelating agent, colorant, UV filter (making it possible to protect the raw materials), pH regulator (acid or base), texturizer, fragrance and/or antioxidant.

By "raw materials to be protected", is meant any component of the cosmetic or dermatological composition capable of being degraded by light.

By "excipient", is meant hydrophilic compounds constituting an aqueous phase, hydrophobic compounds constituting an oil phase or surfactants.

The hydrophilic compounds of the aqueous phase are in particular chosen from water, alcohols and polyols.

The hydrophobic compounds of the oil phase are in particular chosen from the hydrocarbons, fatty acids, fatty alcohols, esters, glycerides, cerides, phosphatides and silicones.

The surfactants are amphiphilic molecules capable of keeping together two media which are normally immiscible with each other by reducing the interfacial tensions. The surfactants are ionic (anionic, cationic or amphoteric) or non-ionic.

The mannoproteins therefore constitute a novel multifunctional natural agent particularly useful for the preparation of cosmetic or dermatological compositions.

The cosmetic or dermatological composition according to the invention contains no polyphenol. In particular, the composition according to the invention contains no dihydroxybenzene, pyrogallol, phloroglucinol, anthocyanidin, proanthocyanidin, flavone, catechin, nor tannin.

A subject of the present invention is also a cosmetic or dermatological composition as defined above, characterized in that it contains no ovomucin.

The cosmetic or dermatological composition according to the invention can comprise, in addition to the mannoproteins as defined above, other yeast constituents.

A subject of the present invention is also a cosmetic or dermatological composition as defined above, characterized in that it contains no filamentous fungus having an altered filamentation property, in particular resulting from an alteration of the gene encoding the CRV1 protein, nor a cell extract of said filamentous fungi.

In another preferred embodiment, a subject of the present invention is a cosmetic or dermatological composition as defined above, characterized in that it comprises no component extracted from fungal cells other than mannoproteins.

A particular subject of the present invention is a cosmetic or dermatological composition as defined above, in which said active ingredient has a moisturizing effect and/or a firming effect and/or an anti-ageing effect and/or an anti-seborrhea effect and/or an anti-acne effect and/or a hair-reconstructing effect and/or an effect on the sheen and/or the softness and/or the growth of the hair.

By the expression "moisturizing effect", is meant a reduction in evaporation from the skin by an occlusive phenomenon or by a fixing of water by the active ingredient, a humectant or hygroscopic effect of the active ingredient and/or a property of fixing of fats in the intercellular cement.

The moisturizing effect of the composition according to the invention results in particular at the level of the epidermis of an activation of the synthesis of lipids, in particular of the phospholipids and of the neutral lipids, and of the synthesis of hyaluronic acid.

The moisturizing effect of the composition according to the invention can be demonstrated in vitro by studying the synthesis of lipids and hyaluronic acid by the keratinocytes, as described in Example 1.

The moisturizing effect of the composition according to the invention also includes an anti-dandruff effect when said composition is applied to the scalp.

The anti-dandruff effect can be demonstrated by a reduction in the amount of dandruff on a subject treated with the composition according to the invention, for example as described in Example 3.

By the expression "firming effect", is meant a smooth and tight appearance of the skin which results from its mechanical support, in particular by collagen and elastin fibres.

The composition according to the invention makes it possible in particular to improve the contraction of the collagen lattice, to activate synthesis of elastin and collagen maturation.

The collagen lattice corresponds to an entanglement of collagen fibres or fibrils.

The firming effect of the composition according to the invention can be demonstrated in vitro as described in Example 1.

By the expression "anti-ageing effect" or "anti-age effect", is meant both a preventive effect for slowing down the appearance of the signs of ageing of the skin and an immediate effect for reducing the signs of ageing. The composition according to the invention has in particular an effect against age-related ageing and can also have an effect against light-induced ageing.

The visible signs of age-related ageing of the skin are in particular a cutaneous dryness, the appearance of fine lines and wrinkles, a reduction in the thickness of the skin, as well as a loss of smoothness of the skin.

The age-related ageing of the skin also involves a reduction in the quantity of collagens, of their solubility and of their synthesis, a reduction in the quantity of elastin and of microfibrils, a reduction in the glycosaminoglycans and an inactivation of the fibroblasts.

The anti-ageing effect of the composition according to the invention results, in particular, from an increase in the activity of the fibroblasts in the dermis in terms of collagen and glycosaminoglycan synthesis.

The anti-age related ageing effect can be demonstrated in vitro by the increase in collagen and glycosaminoglycan synthesis by the fibroblasts of the dermis as described in Example 1.

The signs of light-induced ageing of the skin are, in particular, the appearance of deep wrinkles, a thick and rough skin.

The light-induced ageing of the skin involves in particular a reduction in the quantity and solubility of collagen, an increase in the quantity of elastin and microfibrils, an increase in the glycoaminoglycans, an increase in the inflammatory cells.

A subject of the present invention is also a cosmetic or dermatological composition as defined above, characterized in that the active ingredient has a cicatrizant effect, particularly useful for the repair of injuries and/or burns. The cicatrizant effect of the mannoproteins is in particular linked with the activation of the synthesis of hyaluronic acid.

By the expression "anti-seborrhea effect", is meant an effect of regulating sebaceous secretion, regulating adsorption of the sebum and/or an astringent action making it possible to tighten the pores of the skin.

The composition according to the invention makes it possible to reduce the secretion of sebum.

The composition according to the invention makes it possible in particular to regulate the adsorption of the sebum by lipid adsorption.

The composition according to the invention is thus particularly useful in the context of hyperseborrhea of the face and/or hyperseborrhea of the scalp resulting in so-called "greasy" hair.

The cosmetic composition according to the invention has an anti-seborrhea effect which is useful for greasy skin and/or skin with a tendency to acne.

By the expression "anti-acne effect", is meant an effect which is beneficial vis-à-vis acne.

In particular, the beneficial effect of the dermatological composition according to the invention on acne is linked to a regulation of sebaceous secretion.

By "reconstructive effect", is meant obtaining a smooth appearance of the hair. The outer layer of a hair, called the cuticle, is composed of scales which overlap with each other. A reconstructive effect results in a smooth relief of the cuticle, whereas damaged hairs have a rough relief.

The composition according to the invention has in particular a covering effect on the hair.

The reconstructive effect of the hair can be demonstrated by measuring the topography of the hair, as described in Example 3.

By "sheen effect", is meant the ability of the hair to reflect light, giving the hair a luminous effect.

By "softness effect", is meant the sensation of softness of the hair to the touch.

By "effect on the growth of the hair", is meant an increase in the hair growth kinetics.

The effect on the growth of the hair can be demonstrated by a test which measures the hair growth kinetics, as described in Example 3.

A particular subject of the present invention is a cosmetic or dermatological composition as defined above, in which said additive has a texturizing effect.

By "texturizing agent", is meant an agent capable of increasing the viscosity of the aqueous phases in which it is dispersed, the increase being advantageously high.

A texturizing agent can, depending on the case, be a thickening and/or a gelling agent.

By "thickening agent", is meant a substance which makes it possible to obtain a viscous solution without the formation of a three-dimensional network, as opposed in particular to gelling agents.

The cosmetic or dermatological composition according to the invention can contain several active ingredients, additives and/or excipients.

A subject of the present invention is also a cosmetic or dermatological composition as defined above, in which the mannoproteins are used as active ingredients and additives.

In an advantageous embodiment, the mannoproteins are responsible for both the cosmetic or dermatological effect and the texturizing effect (in the presence of another texturizing product).

A particular subject of the present invention is a cosmetic or dermatological composition as defined above, in which the mannoproteins are also present as surfactant, in particular as emulsifying agent.

By "emulsifying agent" or "emulsifier", is meant a surfactant which is introduced into the composition of an emulsion, said emulsion also comprising a lipophilic phase and a hydrophilic phase. Emulsions are dispersions of one liquid in another liquid, the two liquids being immiscible with each other.

A subject of the present invention is a cosmetic or dermatological composition as defined above comprising mannoproteins as active ingredients and as excipients.

A subject of the present invention is a cosmetic or dermatological composition as defined above comprising mannoproteins as additives and excipients.

A subject of the present invention is also a cosmetic or dermatological composition as defined above comprising mannoproteins as active ingredients, additives and excipients.

In another embodiment of the invention, the mannoproteins have no excipient effect in the cosmetic or dermatological composition. In particular, a subject of the present invention is a cosmetic or dermatological composition as defined above in which the mannoproteins have no surfactant effect, and in particular no emulsifying effect.

A subject of the present invention is a cosmetic or dermatological composition as defined above in the form of solution (a phase), dispersion (in particular an emulsion, suspension, foam or aerosol), gel, oil, stick, powder, wipes or patches.

By "emulsion", is meant any type of emulsion, and in particular a macro-emulsion, micro-emulsion, nano-emulsion, simple emulsion, multiple emulsion.

Emulsions are dispersions of one liquid in another liquid, the two liquids being immiscible. The emulsions comprise a lipophilic and a hydrophilic phase and an emulsifier.

The emulsions include in particular milks, lotions, creams, etc.

Nano-emulsions are dispersions in which the size of the particles dispersed is less than 1000 nm in diameter, in particular from 10 nm to 100 nm.

Micro-emulsions are dispersions in which the size of the dispersed particles is less than 1000 μm in diameter, in particular from 10 μm to 100 μm.

Nano-emulsions and micro-emulsions constitute transparent media.

The cosmetic or dermatological composition according to the invention is in particular appropriate for cutaneous or capillary applications.

The composition according to the invention for capillary applications is in particular in the form of shampoos, lotions, masks, sprays.

A subject of the present invention is a composition as defined above, comprising from 0.01% to 20% mannoproteins, in particular from 0.01% to 15% mannoproteins, in particular from 0.01% to 10% mannoproteins, in particular from 0.01% to 3% mannoproteins.

The percentages are given in weight/weight.

A particular subject of the present invention is a composition as defined above, comprising from 0.01% to 3% mannoproteins, in particular from 0.01% to 2% mannoproteins, as an active ingredient.

A particular subject of the present invention is a composition as defined above, comprising from 0.01% to 20% mannoproteins, in particular from 1 to 20% mannoproteins, in particular from 10% to 20% mannoproteins, in particular from 15% to 20% mannoproteins, as an additive.

A subject of the present invention is also a method for the preparation of a cosmetic or dermatological composition as defined above comprising a stage of mixing the mannoproteins with an acceptable cosmetic or dermatological vehicle.

The acceptable cosmetic or dermatological vehicle is in particular chosen from the abovementioned additives and/or excipients.

A subject of the present invention is also a method for the preparation of a cosmetic or dermatological composition as defined above comprising a stage of mixing the mannoproteins with an acceptable cosmetic or dermatological vehicle and with at least one active ingredient other than mannoproteins.

A subject of the present invention is a cosmetic treatment method comprising a stage of bringing a cosmetic composition as defined above or as obtained by the preparation method defined above into contact with the skin and/or the skin appendages.

The term "bringing into contact" is also referred to as "application" hereafter.

The treatment method can comprise one to several applications daily, preferably one to three applications daily.

The frequency of the applications of the cosmetic composition may be reduced over the course of the treatment.

The cosmetic treatment method can consist of a short-term treatment, of one to several weeks, or a long-term treatment over several years. The treatment method can also consist of a treatment in the form of courses of treatment repeated every year or several times a year.

A particular subject of the present invention is a cosmetic treatment method as defined above, intended to moisturize the epidermis, firm the dermis, combat the ageing of the skin, regulate the secretion of sebum, repair the hair and/or improve the growth of the hair.

The moisturizing of the epidermis is intended both to re-establish the quality of the cutaneous barrier, namely an impermeability limiting the evaporation of water, and to promote the presence of water-trapping molecules, in particular glycosaminoglycans, including hyaluronic acid.

The cosmetic treatment method according to the invention is particularly useful in the treatment and/or prevention of cutaneous dryness and dandruff.

The firming of the dermis is intended to maintain or reinforce the firmness of the dermis, in particular by activating the synthesis of elastin, the synthesis and maturation of collagen and the contraction of the collagen lattice.

The fight against the ageing of the skin has the objective of slowing down and/or reducing the signs of ageing.

In an advantageous embodiment of the invention, the treatment intended to combat ageing is coupled with moisturizing of the epidermis.

The cosmetic treatment method according to the invention is particularly recommended in subjects as from the age of 20 years, in particular 30 years, in particular 40 years, in particular 50 years.

The regulation of the secretion of sebum has in particular the objective of reducing the secretion of sebum.

The cosmetic treatment method according to the invention is particularly useful for regulating seborrhea of greasy skin, in particular for so-called "problem" greasy skin or skin "with a tendency to acne", and/or for so-called "greasy" hair.

The repair of the hair consists in reconstructing the hair, in particular by smoothing the cuticle of the hair and/or in restoring the sheen and/or softness to the hair.

The cosmetic treatment method according to the invention is in particular appropriate in subjects whose hair is damaged, in particular following exposure to the sun, the sea, too-frequent washing, colouring, highlights, perms, etc.

The improvement in the growth of the hair aims to increase the hair growth kinetics, also called growth of the hair.

The cosmetic treatment method according to the invention is in particular appropriate in subjects with slow hair growth kinetics and/or in the case of normal hair loss.

So-called normal hair loss corresponds in particular to male-pattern alopecia, endocrine alopecia, or age-related alopecia.

In an advantageous embodiment, the cosmetic treatment method according to the invention is appropriate for application to the face, in particular around the eyes, the nose, forehead, chin, to the body, in particular to the hands, feet, and back, to the hair and/or scalp.

A subject of the present invention is also the use of mannoproteins for the preparation of a dermatological composition as defined above or as obtained by the above preparation method, intended for the treatment and/or prevention of pathological conditions of cutaneous dryness and/or hyperseborrhea and/or acne and/or hair loss.

The use as defined above is intended for a topical application of said dermatological composition to the skin and/or the skin appendages.

The use as defined above can consist of one or more applications daily, preferably one to three applications daily.

The frequency of the applications of the dermatological composition may be reduced over the course of treatment.

The dermatological treatment can consist of a short-term treatment, of a few days to several weeks, or a long-term treatment over several years. The treatment can also consist of a treatment in the form of courses of treatment repeated every year or several times a year.

In an advantageous embodiment, the dermatological composition comprises mannoproteins as active ingredient, in combination with at least one other active ingredient.

The dermatological composition according to the invention is particularly useful in the treatment of pathological cutaneous dryness of the skin, also called xerosis, in particular in the case of ichthyosis, dryness of the skin associated with eczema or with psoriasis or pathological dryness of the scalp, in particular associated with dandruff.

The dermatological composition according to the invention is also useful in the treatment of pathological hyperseborrhea, in particular associated with a hormonal imbalance, in particular in adolescents and pregnant or menopausal women.

The dermatological composition according to the invention is also useful in the treatment of pathological acne, in particular of juvenile acne or acne associated with hyperseborrhea.

The dermatological composition according to the invention is also useful in the treatment of pathological hair loss, also called alopecia areata, resulting from an emotional shock, thyroid dysfunction and/or treatments resulting in alopecia as a side effect (for example anti-cancer treatment).

In a preferred embodiment, the use of mannoproteins for the preparation of a dermatological composition as defined above is not intended for the treatment of diseases involving neutrophil migration, and in particular diseases associated with IL-8.

A subject of the present invention is also the use of a cosmetic composition or of a dermatological composition as defined above, intended for the treatment of side effects or unpleasant symptoms of other treatments.

In particular, said side effects or unpleasant symptoms include dryness of the skin, for example associated with eczema, hyperseborrhea, or hair loss.

The treatments responsible for said side effects and unpleasant symptoms are for example intended for the treatment of diseases involving neutrophil migration, in particular for the treatment of inflammatory diseases or infections involving regulation by IL-8 (interleukin 8), fMLP (N-formyl-methionyl-leucyl-phenylalanine), PAF (Platelet Activating Factor), C5a (glycoprotein originating from the cleavage of the N-terminal part of the complement), TNFα (Tumor Necrosis Factor α), L-selectin.

A subject of the invention is also the use of mannoproteins as texturizing agents in combination with another texturizing product, in cosmetic and/or dermatological compositions.

A subject of the invention is also compositions as described above, in which the mannoproteins are present in combination with another texturizing product, in particular xanthan gum. The mannoproteins are capable of synergetically increasing the texturizing effect (in particular the ability to increase the viscosity) of other texturizing products, and in particular of xanthan gum. A mannoproteins to xanthan gum mass ratio comprised between 1:5 and 1:3 provides the best synergistic effect. In more particularly preferred manner, this mass ratio is approximately 1:4.

The invention also relates to cosmetic treatment methods as described above, using these compositions.

EXAMPLES

The following examples illustrate the invention without limiting it.

Example 1

Moisturizing, Anti-Ageing and Firmness Properties of Mannoproteins

Material and Methods
(i) Mannoproteins

The mannoproteins obtained according to the method described in the patent EP 1 094117 are put into solution in water and are tested at a concentration of 0.04 mg/ml, 0.08 mg/ml, 0.016 mg/ml or 0.032 mg/ml.

(ii) Moisturizing Effect

The tests are carried out on normal human epidermal keratinocytes NHEKs seeded in the wells of a 96-well microplate in KSFM medium (serum-free). The synthesis of lipids and the synthesis of hyaluronic acid are evaluated in the presence of the different concentrations of mannoproteins. Three culture wells are produced per condition.

Calcium is used as a positive control of the synthesis of lipids and retinoic acid as a positive control of the synthesis of hyaluronic acid.

The negative control is constituted by culture medium alone.

The synthesis of hyaluronic acid is evaluated in the supernatant at the end of incubation (72 hours at 37° C. and 5% $CO_2$) by a standard ELISA assay, according to the manufacturer's instructions (R&D Systems DY3614).

The synthesis of lipids is analyzed by phosphor imaging and the synthesis of hyaluronic acid is evaluated by a measurement of the concentration of hyaluronic acid released in the medium.

(iii) Anti-ageing effect

Normal human dermal fibroblasts (NHDF) and aged normal human dermal fibroblasts (AgNHDF) are seeded in the wells of a 96-well microplate in DMEM medium+10% FCS. The tests are carried out in DMEM medium+1% FCS. The two media are also supplemented with 2 mM of L-glutamine, 50 UI/mL of penicillin and 50 µg/mL of streptomycin. The FCS (foetal calf serum), L-glutamine, penicillin and streptomycin are obtained from Invitrogen. The culture is carried out at 37° C. and at 5% $CO_2$. The normal fibroblasts are fibroblasts from pool F2 at the $8^{th}$ passage, and the aged fibroblasts are fibroblasts from pool F2 at the $18^{th}$ passage.

The proliferation test of the fibroblasts and the glycosaminoglycan and collagen synthesis test are carried out in the presence of different concentrations of mannoproteins. Three culture wells are produced per condition.

The negative control is constituted by culture medium alone.

The proliferation test is carried out 24 hours after seeding the cells. [$^3$H]-thymidine is added to the culture medium. EGF is used as positive control.

The synthesis of glycosaminoglycan and of collagen is evaluated on cells at 80% confluence to which [$^3$H]-glucosamine or [$^3$H]-proline are added respectively. Retinoic acid is then used as positive control.

After incubation for 72 hours, the macromolecules are extracted and the incorporation of the radioactive precursors is measured. As regards the incorporation of proline, a distinction is drawn between incorporation in the supernatant (soluble fraction) and in the intracellular and deposited fraction.

(iv) Firming Effect

The tests are carried out on aged normal human dermal fibroblasts (AgNHDF).

The synthesis and maturation of the collagen are evaluated after preculture of the cells in a flask for 8 days in the presence of different concentrations of mannoproteins. The negative control is constituted by culture medium alone and the positive control by TGFβ and vitamin C. The cells are then seeded in a culture chamber. Just before confluence, the cells are fixed with methanol and the presence of collagen is detected by immunohistochemistry using a specific antibody directed against collagen I and a fluorescent secondary antibody. The level of expression of the intracellular and extracellular collagen and its location around the matrix are analyzed with a microscope.

The contraction of the collagen lattice is evaluated after culture of the cells in a flask for 8 days in the presence of different concentrations of mannoproteins. The negative control is constituted by culture medium alone and the positive control by TGFβ. The cell suspension obtained is then brought together with a solution of collagen I under controlled pH. After a few hours, the solution gels so as to obtain an equivalent dermis the contour of which is clearly defined. The diameter and the number of cells of each equivalent dermis are measured according to defined kinetics.

The synthesis of elastin is evaluated after culture of the cells in a flask for 8 days in the presence of different concentrations of mannoproteins. The negative control is constituted by culture medium alone and the positive control by vitamin C. The cells are then seeded in culture chambers. Just before confluence, the cells are fixed with methanol and the presence of elastin is detected by immunohistochemistry using a specific antibody directed against the elastin and a fluorescent secondary antibody. The level of expression of elastin is analyzed with a microscope.

(v) Statistics

Intergroup comparisons are carried out by analysis of variance (ANOVA) using a Dunnett multiple comparison test Results i) Evaluation of the Moisturizing Effect on the Epidermis In the presence of the solution of mannoproteins, the synthesis of lipids and of hyaluronic acid by the keratinocytes is activated with respect to the negative control.

In particular, when the keratinocytes are subjected to a concentration of 0.032 mg/mL of mannoproteins, a 151% stimulation of hyaluronic acid production is obtained with respect to the negative control (the test being judged significant as the p value is less than 0.05).

ii) Evaluation of the Anti-Ageing Effect on the Dermis

In the presence of the solution of mannoproteins, an increase in the synthesis of the major constituents of the extracellular matrix (with respect to the negative control) is observed.

In particular, the results presented in Table 1 below are obtained with respect to the synthesis of collagen:

TABLE 1

Synthesis of collagen observed in the presence of mannoproteins (MP)

| Test conditions | Variation in the synthesis of collagen with respect to the negative control | p value |
|---|---|---|
| NHDF, 80 µg/mL MP, measured on supernatant | +7% | <0.05 |
| NHDF, 400 µg/mL MP, measured on supernatant | +8% | <0.05 |

TABLE 1-continued

Synthesis of collagen observed in the presence of mannoproteins (MP)

| Test conditions | Variation in the synthesis of collagen with respect to the negative control | p value |
|---|---|---|
| AgNHDF, 16 µg/mL MP, measured on supernatant | +12% | <0.05 |
| AgNHDF, 80 µg/mL MP, measured on supernatant | +10% | <0.05 |
| AgNHDF, 400 µg/mL MP, measured on supernatant | +26% | <0.01 |
| AgNHDF, 16 µg/mL MP, measured on deposit | +1% | <0.05 |
| AgNHDF, 80 µg/mL MP, measured on deposit | +5% | <0.05 |
| AgNHDF, 400 µg/mL MP, measured on deposit | +7% | <0.05 |

Moreover the results presented in Table 2 below with respect to the synthesis of glycosaminoglycan (GAG) are obtained:

TABLE 2

Synthesis of glycosaminoglycan observed in the presence of mannoproteins (MP)

| Test conditions | Variation in the synthesis of GAG with respect to the negative control | p value |
|---|---|---|
| NHDF, 80 µg/mL MP | +6% | <0.05 |
| AgNHDF, 80 µg/mL MP | +22% | <0.05 |
| AgNHDF, 400 µg/mL MP | +10% | <0.05 | iii) Evaluation of the Firming Effect on the Dermis

In the presence of the solution of mannoproteins, an increase in the level of expression of the collagen is observed, as well as a maturation of the collagen revealed by its deposition around the matrix, with respect to the negative control. The increase in the density of the equivalent dermis (diameter to number of cells ratio lower than that of the negative control) results in a better contraction of the collagen lattice. Furthermore, the synthesis of elastin by the fibroblasts is activated with respect to the negative control. All these elements indicate that the mannoproteins improve the biomechanical qualities of the dermis (in particular in terms of elasticity and of compressibility).

Example 2

Anti-Seborrhea and Anti-Acne Properties

Material and Methods

The solution of mannoproteins is applied to the skin or the scalp of subjects having a hyperseborrhea of the skin or of the scalp respectively.

The secretion of sebum is then evaluated by applying a sebum-absorbing patch to the part of the body treated. The patch is then analyzed in order to quantify the sebaceous secretion.

The secretion after treatment is compared to the secretion in the same subject before treatment.

Results

The solution of mannoproteins makes it possible to reduce the quantity of sebum secreted.

Example 3

Capillary Applications

Material and Methods (i) Mannoproteins

The mannoproteins obtained according to the method described in the patent EP 1 094 117 are put into solution in water.

(ii) Anti-Dandruff Effect

The solution of mannoproteins is applied to the scalp of subjects suffering from dandruff. After treatment with the solution of mannoproteins, a patch is applied only to the area treated in order to recover the dandruff from the scalp.

The quantity of dandruff recovered on the patch is compared before and after treatment.

(iii) Hair Growth

Evaluation of the hair growth kinetics takes place as follows: before treatment, a strand of a subject's hair is coloured from the root over 2-3 cm; the solution of mannoproteins is then applied to the scalp; the distance between the root and the start of the coloration is measured.

The growth kinetics after treatment of a group of treated subjects is compared with that obtained with a group of untreated subjects.

(iv) Sheen of the Hair

The sheen of the hair is determined by measuring the quantity and the intensity of the light reflected at the surface of the hair. To this end, cross-polarized and non-polarized photographs of the hair are taken. The two photographs are then converted to grey scale and the sheen of the hair is obtained by subtraction of the light between the two photographs.

The sheen of the hair after application of the solution of mannoproteins is compared with that obtained before treatment.

(v) Softness of the Hair

The softness of the hair is evaluated using sensory analysis by a jury constituted by three individuals qualified to evaluate the softness of the hair to the touch.

The softness of the hair is marked on a scale of 0 to 10, with 0 corresponding to an absence of softness and 10 to a very great softness.

The softness of the hair after application of the solution of mannoproteins is compared to that obtained before treatment.

(vi) Reconstruction of the Hair

The reconstruction of the hair is evaluated by measuring the surface topography of the hair using an interferometric microscope.

The parameters making it possible to determine the condition of the scales of the cuticle along the hair are as follows:

opening of the scales,
length of the scales and
surface topology, namely roughness.

The surface analyzed measures 120×30 µm.

The reconstruction of the hair after application of the solution of mannoproteins is compared with the state of the hair before treatment.

Results

The capillary application of the solution of mannoproteins makes it possible to obtain an anti-dandruff effect and an increase in hair growth.

The solution of mannoproteins also has a remedial effect on the hair, making it possible to improve the sheen, the softness and the reconstruction of the hair. In particular, a reduction in the number of openings in the scales of the cuticle, an increase in the length of the scales and a reduction in the roughness are noted.

Example 4

Function of Texturizing Additive and Emulsifying Excipient

Material and Method (i) Mannoproteins

The mannoproteins obtained according to the process described in the patent EP 1 094 117 are put into solution in water, (ii) Texturizing Character The texturizing character and the film formation properties of the mannoproteins are evaluated by different methods: analysis of the size of the particles by measurement of laser light scattering, rheology studies (yield value, viscosity and tan d (also called DMA)), stability tests (conductivity, granulometry, viscosity, colour and fragrance) at different temperatures and durations, microscopy and spreading over the skin.

The texturizing effect of the mannoproteins in aqueous formulations is compared with xanthan gum (natural polysaccharide) and with carbomers.

The compatibility of the mannoproteins with different emulsifying systems is also tested. These emulsifying systems are:

an anionic system: Ceralution H,
a non-ionic system: Tego Care 450,
a sun-filter lotion with $TiO_2$, based on a non-ionic system,
and a gel.

The gel system makes it possible to test the emulsifying properties of the mannoproteins.

Results

Polymeric texturizers are widely used in cosmetic formulations. These texturizers are key products for producing cream, gel and lotion type formulations, etc. The texturizers must retain their properties in the presence of a wide range of chemical additives.

The use of mannoproteins in formulations with water has been compared with the use of standard texturizing products (hydrophilic additives such as xanthan gum or carbomers). The mannoproteins have also been tested in different emulsifying systems.

The mannoproteins are compatible with standard emulsifying systems. The mannoproteins are also capable of forming films and act as polymeric emulsifiers.

It has moreover been noted that the mannoproteins can have a texturizing effect synergistically with certain other texturizing products, such as xanthan gum. Table 3 below provides viscosity measurement results for a solution comprising water, xanthan gum and mannoproteins in various concentrations.

TABLE 3

Rheology of solutions of water/xanthan gum (XG)/mannoproteins (MP).

| Composition of the solution tested | Viscosity in mPas |
|---|---|
| 0% MP + 1% XG + 99% water | 4460 |
| 0.2% MP + 0.8% XG + 99% water | 8752 |
| 0.5% MP + 0.5% XG + 99% water | 4127 |
| 0% MP + 0.5% XG + 99.5% water | 2460 |
| 0.1% MP + 0.4% XG + 99.5% water | 2995 |
| 0.25% MP + 0.25% XG + 99.5% water | 1022 |

The invention claimed is:

1. A topical cosmetic and/or dermatological composition for topical application to skin and/or hair consisting of mannoproteins extracted from the cell walls of *Saccharomyces* as a texturizing agent in combination with xanthan gum as another texturizing agent, the mannoproteins are present in the composition in a mass ratio of mannoproteins to xanthan gum of 1:4 such that the mannoproteins synergetically effect the xanthan gum by increasing the texturizing effect thereof so that the composition is provided with increased viscosity to improve the skin and/or hair to which it is applied, the composition consisting of 0.2% mannoproteins to 0.8% xanthan gum based on a weight of said composition to provide the composition with a viscosity of 8752 mPas, the composition containing no polyphenols nor ovomucin.

2. The composition of claim 1 wherein the mannoproteins originate from *Saccharomyces cerevisiae*.

3. The composition of claim 1 wherein the composition contains no dihydroxybenzene, pyrogallol, phloroglucinol, anthocyanidin, proanthocyanidin, flavone, catechin, tannin, or no filamentous fungus.

4. The composition of claim 1 wherein the mannoproteins has a protein content ranging from about 25.6% to about 43%.

* * * * *